US012758092B2

(12) United States Patent
Wang et al.

(10) Patent No.: US 12,758,092 B2
(45) Date of Patent: Oct. 13, 2026

(54) SYSTEM AND METHOD FOR ASSISTING A SUBJECT WITH ALIGNMENT TO AN OPHTHALMOLOGIC DEVICE

(71) Applicants: Carl Zeiss Meditec, Inc., Dublin, CA (US); Carl Zeiss Meditec AG, Jena (DE)

(72) Inventors: Yingjian Wang, Fremont, CA (US); Jochen Straub, Pleasanton, CA (US); Conor Leahy, Dublin, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 116 days.

(21) Appl. No.: 18/714,067

(22) PCT Filed: Dec. 14, 2022

(86) PCT No.: PCT/EP2022/085846

§ 371 (c)(1),
(2) Date: May 28, 2024

(87) PCT Pub. No.: WO2023/111014

PCT Pub. Date: Jun. 22, 2023

(65) Prior Publication Data

US 2025/0017462 A1 Jan. 16, 2025

Related U.S. Application Data

(60) Provisional application No. 63/290,044, filed on Dec. 15, 2021.

(51) Int. Cl.

*A61B 3/00* (2006.01)
*A61B 3/10* (2006.01)

(Continued)

(52) U.S. Cl.

CPC ............ *A61B 3/0091* (2013.01); *A61B 3/102* (2013.01); *A61B 3/1225* (2013.01); *A61B 3/152* (2013.01)

(58) Field of Classification Search

CPC ..... A61B 3/0091; A61B 3/102; A61B 3/1225; A61B 3/152; A61B 3/0083; A61B 3/12

See application file for complete search history.

(56) References Cited

U.S. PATENT DOCUMENTS 8,573,776 B2 * 11/2013 Koizumi ................ A61B 3/102
351/208
8,646,913 B2 * 2/2014 Hayashi ............ G01B 9/02044
351/208

(Continued)

FOREIGN PATENT DOCUMENTS

EP 2374404 10/2011
EP 2752151 7/2014

(Continued)

OTHER PUBLICATIONS

International Search Authority; International Search Report and Written Opinion dated Jun. 3, 2023 in Application No. PCT/EP2022/085846.

*Primary Examiner* — Tuyen Tra
(74) *Attorney, Agent, or Firm* — SNELL & WILMER L.L.P.

(57) ABSTRACT

A system for assisting a subject with alignment with an ophthalmologic device that includes a first light source and an image sensor. The system includes first and second fixation targets located in a first plane to transmit light having first and second optical characteristics. Also, first and second apertures are located in a second plane and configured to spatially filter the light transmitted from the first and second fixation targets. At least one lens configured to image the first and second apertures in the second plane to a third (Continued)

plane approximately corresponding to the subject's pupil, wherein, based upon the ophthalmologic device being misaligned with the subject's pupil in the third plane, the subject's retina receives an image of at most one of the first and second fixation targets.

26 Claims, 6 Drawing Sheets

(51) Int. Cl.

| | |
|---|---|
| ***A61B 3/12*** | (2006.01) |
| ***A61B 3/15*** | (2006.01) |

(56) References Cited

U.S. PATENT DOCUMENTS

| | | | | |
|---|---|---|---|---|
| 8,931,901 | B2 | 1/2015 | Ikegami | |
| 2007/0258045 | A1 | 11/2007 | Yamaguchi et al. | |
| 2015/0103355 | A1 | 4/2015 | Bower et al. | |
| 2016/0367134 | A1* | 12/2016 | Su | A61B 3/12 |
| 2018/0008143 | A1 | 1/2018 | Chong | |
| 2021/0076921 | A1 | 3/2021 | Nagae et al. | |

FOREIGN PATENT DOCUMENTS

| | | |
|---|---|---|
| EP | 3607871 | 2/2020 |
| JP | 6585897 | 10/2019 |
| WO | 2007146714 | 12/2007 |
| WO | 2017025583 | 2/2017 |
| WO | 2023111014 | 6/2023 |

* cited by examiner

SYSTEM AND METHOD FOR ASSISTING A SUBJECT WITH ALIGNMENT TO AN OPHTHALMOLOGIC DEVICE

CROSS REFERENCE TO RELATED APPLICATIONS

This application is a U.S. national stage entry under 35 U.S.C. § 371 of International Application No. PCT/EP2022/085846 filed Dec. 14, 2022 entitled “SYSTEM AND METHOD FOR ASSISTING A SUBJECT WITH ALIGNMENT TO AN OPHTHALMOLOGIC DEVICE” The ’846 PCT claims priority to, and the benefit of, U.S. Provisional Application Ser. No. 63/290,044 filed Dec. 15, 2021, entitled “SELF-ALIGNMENT FIXATION” Each of the foregoing applications are hereby incorporated by reference in their entirety for all purposes.

FIELD OF INVENTION

The present invention is generally directed to the field of ophthalmologic imaging systems. More specifically, it is directed to self-alignment techniques for facilitating user operation of an ophthalmologic imaging system.

BACKGROUND

Subject pupil alignment is necessary to obtain acceptable image quality using ophthalmologic devices. The alignment process is traditionally done by an ophthalmologic technician or by an automated system, which in the former case requires operator training and in the latter case can entail additional costs in the manufacturing process which may be passed along to the purchaser. For Optical Coherence Tomography (OCT) devices, to obtain a good image, it is desirable for an illuminating strip to pass unabated through the pupil, and reach the fundus, of an eye. This requires careful alignment of the eye with the ophthalmologic imager (or other ophthalmologic examination systems) of the OCT device. Consequently, more training of an operator of the device is generally needed to achieve a high level of competency in using such OCT systems.

It is desirable to reduce costs in operating OCT devices by implementing a mechanism for self-alignment without an operator having to monitor the subject’s pupil and align the fundus camera prior to taking an image of the subject’s retina.

It is desirable to implement automated feedback mechanisms to enable a subject to monitor the pupil for alignment without the assistance of the operator.

It is desirable to implement the use of a fixation target to guide a subject’s gaze to enable an initial alignment of an ophthalmologic device to the subject’s pupil that saves time and eliminates additional training of the operator to perform this step when operating the specialty (e.g., OCT) device.

It is desirable to implement self-alignment for a home care ophthalmologic device including but not limited to OCT and fundus imaging devices that the subject can self-align and fixate themselves before the device takes OCT or fundus images without clinicians around.

It is desirable to enable fully or semi-remote-controlled OCT with self-alignment features to protect a subject and clinician from the spread of viruses in a siloed or more isolated environment for the imaging operation process.

It is at least an object of the present invention to provide a system and method to facilitate subject self-alignment and fixation of an ophthalmologic system, such as an OCT system.

SUMMARY

In an embodiment, a system for assisting a subject with alignment with an ophthalmologic device comprising a first light source and an image sensor is provided. The system includes first and second fixation targets located in a first plane and respectively configured to transmit light having first and second optical characteristics; first and second apertures located in a second plane and configured to spatially filter the light transmitted from the first and second fixation targets; first and second filters located approximately in the second plane, the first filter configured to optically filter the spatially filtered light from the first fixation target to have the first optical characteristic, the second filter configured to optically filter the spatially filtered light from the second fixation target to have the second optical characteristic; and at least one lens configured to image the first and second apertures in the second plane to a third plane approximately corresponding to the subject’s pupil, wherein, based upon the ophthalmologic device being misaligned with the subject’s pupil in approximately the third plane, the subject’s pupil blocks the image of at least one of the first and second apertures such that the subject’s retina receives an image of at most one of the first and second fixation targets; and wherein, based upon the ophthalmologic device being aligned with the subject’s pupil in approximately the third plane: the subject’s pupil substantially transmits the images of the first and second apertures such that the subject’s retina receives an image of the first and second fixation targets, and light from the first light source of the ophthalmologic device enters the subject’s pupil, is reflected or scattered by the subject’s retina, exits the subject’s pupil, and is received by the image sensor.

In various exemplary embodiments, the third plane, the image of the first and second fixation targets forms a set of endpoints to the light from the first light source.

In various exemplary embodiments, the first and second optical characteristics comprise different colors from one another.

In various exemplary embodiments, the first and second fixation targets respectively comprise different color filters.

In various exemplary embodiments, the first optical characteristic comprises a red color, and wherein the second optical characteristic comprises a blue color.

In various exemplary embodiments, the first and second filters respectively comprise different color filters.

In various exemplary embodiments, the first and second optical characteristics comprise different polarizations than one another.

In various exemplary embodiments, the first and second fixation targets respectively comprise different polarization filters than one another.

In various exemplary embodiments, the first and second filters respectively comprise different polarization filters.

In various exemplary embodiments, the light from the first light source comprises a line segment in the third plane.

In various exemplary embodiments, the line segment has a length that is approximately equal to the width of the pupil.

In various exemplary embodiments, the length of the line segment is in a range of about 1.8 mm to 2.0 mm.

In various exemplary embodiments, the system further includes a second light source generating the light transmitted by the first and second fixation targets.

In various exemplary embodiments, the second light source generates coherent light.

In various exemplary embodiments, the second light source generates non-coherent light.

In various exemplary embodiments, the system further includes an objective lens disposed between the first plane and the second plane, the objective lens is configured to project the first and second fixation targets at infinity through the first and second apertures.

In various exemplary embodiments, at least one lens comprises a pupil relay lens disposed between the second plane and the third plane, the pupil relay lens being configured to image the first and second apertures into the third plane.

In various exemplary embodiments, the system further comprises a beam splitter configured to transmit light from the first light source, to reflect light having the first optical characteristic, and to reflect light having the second optical characteristic.

In various exemplary embodiments, the ophthalmologic device comprises an optical coherence tomography imager.

In various exemplary embodiments, the ophthalmologic device comprises a fundus imager.

In various exemplary embodiments, the system further comprises at least one additional fixation target, at least one additional aperture, and at least one additional filter.

In various exemplary embodiments, a method for assisting a subject with alignment with an ophthalmologic device is provided. The method includes respectively transmitting light having first and second optical characteristics from first and second fixation targets located in a first plane; spatially filtering the light transmitted from the first and second fixation targets using first and second apertures located in a second plane; optically filtering the spatially filtered light from the first fixation target to have the first optical characteristic; optically filtering the spatially filtered light from the second fixation target to have the second optical characteristic; and imaging the first and second apertures in the second plane to a third plane approximately corresponding to the subject's pupil, using at least one lens, wherein, based upon the ophthalmologic device being misaligned with the subject's pupil in approximately the third plane, the subject's pupil blocks the image of at least one of the first and second apertures such that the subject's retina receives an image of at most one of the first and second fixation targets; and wherein, based upon the ophthalmologic device being aligned with the subject's pupil in approximately the third plane: the subject's pupil substantially transmits the images of the first and second apertures such that the subject's retina receives an image of the first and second fixation targets, and light from the first light source of the ophthalmologic device enters the subject's pupil, is reflected or scattered by the subject's retina, exits the subject's pupil, and is received by the image sensor.

In various exemplary embodiments, a system for assisting a subject with alignment with an ophthalmologic device comprising a light source and an image sensor is provided. The system includes a source of coherent light located in a first plane; first and second apertures located in a second plane and configured to spatially filter the light transmitted from the source of coherent light; and at least one lens configured to image the first and second apertures in the second plane to a third plane approximately corresponding to the subject's pupil, wherein, based upon the ophthalmologic device being misaligned with the subject's pupil in approximately the third plane, the subject's pupil blocks the image of at least one of the first and second apertures such that the subject's retina receives light from at most one of the first and second apertures; and wherein, based upon the ophthalmologic device being aligned with the subject's pupil in approximately the third plane: the subject's pupil substantially transmits the images of the first and second apertures such that the subject's retina receives an interference pattern generated by light from the first and second apertures, and light from the light source of the ophthalmologic device enters the subject's pupil, is reflected or scattered by the subject's retina, exits the subject's pupil, and is received by the image sensor.

In various exemplary embodiments, the interference pattern comprises a vertical line pattern.

In various exemplary embodiments, when the subject's retina receives light from at most one of the first and second apertures, the subject's retina receives a uniform color background.

In various exemplary embodiments, a method for assisting a subject with alignment with an ophthalmologic device comprising a light source and an image sensor is provided. The system includes spatially filtering coherent light transmitted from a source in a first plane using first and second apertures located in a second plane; and imaging the first and second apertures in the second plane to a third plane approximately corresponding to the subject's pupil, wherein, based upon the ophthalmologic device being misaligned with the subject's pupil in approximately the third plane, the subject's pupil blocks the image of at least one of the first and second apertures such that the subject's retina receives light from at most one of the first and second apertures; and wherein, based upon the ophthalmologic device being aligned with the subject's pupil in approximately the third plane: the subject's pupil substantially transmits the images of the first and second apertures such that the subject's retina receives an interference pattern generated by light from the first and second apertures, and light from the light source of the ophthalmologic device enters the subject's pupil, is reflected or scattered by the subject's retina, exits the subject's pupil, and is received by the image sensor.

The foregoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1:
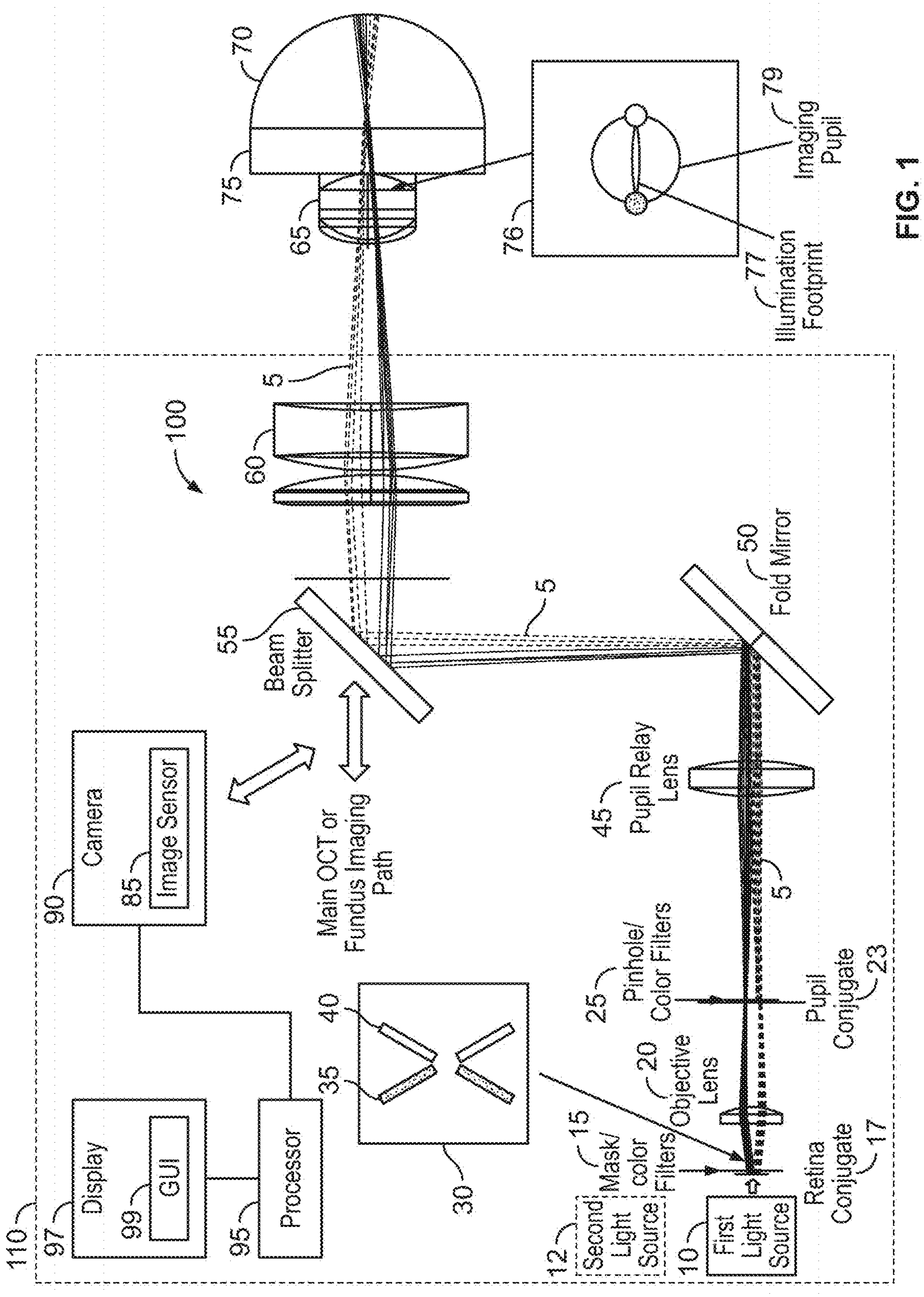
FIG. 1 illustrates an example diagram of a self-alignment fixation system integrated into an OCT, fundus imaging, or other ophthalmologic device in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not for limitation. Furthermore, any reference to singular includes plural embodiments, and any reference to more than one component or step may include a singular embodiment or step. Also, any reference to attached, fixed, connected, or the like may include permanent, removable, temporary, partial, full, or any other possible attachment option. Additionally, any reference to without contact (or similar phrases) may also include reduced contact or minimal contact. It should also be understood that unless specifically stated otherwise, references to "a," "an" or "the" may include one or more than one, and that reference to an item in the singular may also include the item in the plural. Further, all ranges may include upper and lower values, and all ranges and ratio limits disclosed herein may be combined.

Ophthalmologic systems and devices need to be aligned relative to a subject's eye and particularly may require the alignment of a subject's pupil. Although different ophthalmologic systems have different levels of alignment requirements, all require some level of alignment, and some have very high alignment requirements for proper operation. Some ophthalmologic systems place alignment requirements on the pupil of a subject's eye with sub-millimeter accuracy in three spatial dimensions. Typically, the higher the alignment requirements, the more complicated/involved the system procedures to achieve precise alignment. In such cases, the alignment task is traditionally performed by an ophthalmologic technician or by an automated positioning system.

System-to-subject alignment can be difficult to achieve, particularly when it is desirable for the system to support self-administered ophthalmologic procedures, such as for at-home, portable, remote-controlled, and/or personal use. Such systems cannot rely on an operator to provide the system-to-subject alignment. Furthermore, such systems often have low-cost requirements, which can severely limit the use of automated alignment sub-systems since they typically are complex, expensive, and prone to reliability problems.

Various types of ophthalmologic systems/devices are known, and they are often used for diagnostic and/or therapeutic (e.g., treatment) purposes. Examples of ophthalmologic therapeutic systems/devices may be an ophthalmologic medication delivery system (manual, automated, or semi-automated systems) or an ophthalmologic treatment system such as a system used in an ophthalmologic medical procedure, e.g., ophthalmologic laser surgery. Examples of ophthalmologic diagnostic systems/devices may include visual field test perimeters, autorefractors, corneal pachymeters, ophthalmologic ultrasound devices, slit lamps, tonometers, surgical apparatuses/tools, and various ophthalmologic imaging systems. Ophthalmologic devices require some alignment of the device to a subject's eye, with some devices having more critical alignment requirements than others. Herein is presented a self-alignment system/method suitable for ophthalmologic systems but also capable of repeatably and consistently providing high levels of eye alignment for more critical applications.

Although the present invention is not limited to any specific type of ophthalmologic system (diagnostic and/or therapeutic), for the sake of brevity, the present discussion relates to ophthalmologic imaging systems as exemplary systems using the present invention with the understanding that the present invention may be applied to other types of ophthalmologic systems, such as visual field test perimeters, etc.

In various exemplary embodiments, the present invention may apply to OCT imaging performed using commercially available OCT devices with remote desktop access software and consumer video conferencing technology on smartphones and tables that enable separation from the patient and operator for reducing the spread of communicable viruses.

One example of an ophthalmologic imaging system is a fundus imager, which is typically used to image the fundus (or retina) of an eye. The fundus is the interior surface of the eye opposite the eye lens (or crystalline lens) and may include the retina, optic disc, macula, fovea, and posterior pole. Two categories of fundus imagers used to image the fundus are flood illumination imagers and scan imagers. Scan imagers may further be divided into confocal point scanning fundus imagers and line scanning imagers. Another example of an ophthalmologic imaging device is an optical coherence tomography (OCT) system, which permits in situ real-time cross-sectional (e.g., depth) imaging of tissue, e.g., imaging of the anterior or posterior of an eye. OCT systems measure the scattering profile of an OCT beam as it impacts a sample (e.g., the eye fundus), and can construct one-dimensional (1D) depth information at a single point, two-dimensional (2D) cross-sectional images and end face images, and three-dimensional (3D) volume images. Multiple OCT images may be taken at the same location and processed to extract motion information, such as fluid (e.g., blood) flow. OCT systems that extract blood flow information may be termed OCT Angiography (OCTA) systems.

Irrespective of the type of ophthalmologic system, correct alignment of the human eye to the ophthalmologic diagnostic system can be critical to performance. For example, correctly aligning the pupil of the eye to the exit pupil (or aperture) of an ophthalmologic imaging system is critical for imaging the human retina with fundus cameras or OCT systems. In Fundus Imagers, this is complicated by the need to divide an imaging system's aperture into an illumination pupil through which light enters the eye and a collection pupil through which light exiting the eye is collected for imaging (e.g., for collecting image data). Typical ophthalmologic imaging systems are usually operated by a technician who uses various feedback mechanisms and alignment aides to position the ophthalmologic imaging system, which is typically mounted on an adjustable mechanical stage, relative to a subject whose head is held in a fixed position by a rigid chinrest. Automatic control systems that use various feedback mechanisms for alignment have been shown, but such automated systems increase system complexity, and cost, and require regular maintenance for ideal performance.

Smaller, lower-cost, portable, or handheld ophthalmologic imaging systems have been proposed. But such systems still require a trained operator, and typically also require the use of eyecups, and stabilizing bars to achieve repeatable positioning of the imaging systems to the subject's eye. Further complicating their use, lower-cost portable systems have a reduced set of alignment aids for the operator and require more skill to achieve good image data.

A large fraction of the cost of ophthalmologic imaging systems devices goes towards the achievement of device-to-subject alignment both in terms of mechanical placement of the imaging device relative to the eye, and alignment aides which help the operator and/or automated system know how to move the device to achieve the best alignment.

In various exemplary embodiments, in a self-alignment approach, a subject moves/herself and/or the imaging device to achieve alignment between the two. Generally, to facilitate self-alignment, it is desirable that the imaging system have alignment aids to provide the subject with feedback to make the correct alignment changes with minimal effort and training and acquire a good measurement with high repeatability. Such systems require collaboration (e.g., willing cooperation) from the subject, including but not limited to physical movement and mental processing of feedback. A situation where this approach is desirable is for personal, remote, and/or at-home care.

Home care, and/or assisted living care are set to become an increasingly important market as the need for at-home solutions increases, particularly as the cost of various parts of ophthalmologic diagnostic systems (e.g., digital cameras and computing equipment) goes down. Home care presents a special case in which an auxiliary operator (e.g., technician) is less likely to be available to help acquire the image data. Here, the subject and ophthalmologic diagnostic system must work together to acquire good data without dramatically increasing cost or decreasing ease of use.

To aid alignment, ophthalmologic imaging systems generally provide several forms of visual stimuli to the eye of a person whose retina is being imaged. Good alignment may require that: the pupil of the eye be positioned accurately in three dimensions relative to the system's illumination pupil (aperture) and collection pupil (aperture); the gaze of the eye is in the correct angular direction; and the retina is in focus. Imaging systems can provide alignment aids (e.g., feedback mechanisms) for only the illumination pupil of the system.

When a device is properly aligned, this light may cover a region of the retina slightly wider than the field of view of the imaging system. When a subject approaches the aperture of the system from a distance, the subject can visualize the illumination pupil of the camera as an illuminated virtual object, a few millimeters in diameter, apparently floating in space a few centimeters beyond the objective lens of the imaging system. As the subject comes closer to correct alignment, looking into the fundus camera and moving his eye towards superimposition with the illuminated virtual object, it becomes impossible to focus on that virtual object, and the subject may begin to see the shadow of his own eye pupil, as illuminated by the virtual object near the eye. This may seem to the subject as a circularly illuminated field that increases in size as the subject approaches the correct axial location, and shifts in lateral position depending on the lateral alignment. When the subject successfully places the eye such that the illumination reaches a maximum field size and maximum brightness, the pupil of the eye may be assumed to be aligned regarding the illumination pupil of the imaging system and most of the light is passing through uninhibited.

Ophthalmologic systems need to be aligned relative to the pupil of the subject's eye with sub-millimeter accuracy in three dimensions. This task has traditionally been performed by a trained ophthalmologic technician, and/or may be facilitated by an automated positioning system. Both of these approaches introduce complexity and cost constraints, and neither lend themselves easily to self-administered ophthalmologic procedures, such as for at-home use (home care). A subject at home cannot rely on an operator (e.g., visiting technician) to provide machine alignment, and automated systems are complex, expensive, and prone to reliability problems, which a subject cannot be expected to address. Previous self-alignment approaches still tend to be complicated, unreliable, and often difficult for the elderly and incapacitated to achieve.

In preferred embodiments described herein will be focused on the field of Optical Coherence Tomography (OCT). OCT is a non-invasive, in-vivo imaging technique that is based on the back-scatter or reflectivity of light in a medium. OCT is particularly valuable in ophthalmologic examinations, where the beam of light produced by the OCT device scans the eye through the pupil and the image formation process records the back-scattering profile of the light at each location. The intensity of the back-scattered light indicates the scattering properties of the tissue and tissue boundaries, and a grayscale cross-sectional image is formed as the light beam Sweeps across the field of view (FOV). OCT imaging has dramatically advanced ophthalmologic diagnostic capabilities and led also to a better understanding of ocular anatomy. It is the basis of routine ophthalmologic practice.

In various exemplary embodiments, the present disclosure describes systems and methods of self-alignment that implement a simple and easy-to-implement optics layout that can provide immediate and intuitive feedback to the subject under test to ensure their pupil is aligned with the pupil's aperture.

In various exemplary embodiments, the present disclosure describes systems and methods that use spectral or polarization split pupil imaging with the spectral or polarization matching with fixation targets for easy setup and intuitive feedback to the subject. For example, the subject will lose part of the features of the fixation target before the OCT or fundus imaging probing beam is vignetted by their own pupil.

FIG. 1 illustrates an example diagram of a self-alignment fixation module ("fixation module") 100 integrated into an OCT, fundus imaging, or other ophthalmologic devices 110 in accordance with various embodiments. In FIG. 1, there is shown an exemplary implementation of a fixation module 100 which is integrated into the OCT/Fundus imaging or other paths via a beam splitter of an OCT device.

In FIG. 1, the fixation module 100 includes a light source 10 such as an LED that may be an optional light source in addition to a primary light source used for imaging in an ophthalmologic device. Optionally, there may be configured with the fixation module 100 a second light source 12 (e.g., a coherent or non-coherent light source) for alternate modes of self-alignment operation. The light source 10 is configured to at least partially follow an axial optical path (i.e., the main OCT or fundus imaging path) along illumination path 5 that is conveyed through various lenses to the sample or specimen (i.e., retina 70 of the eye 75) to be imaged.

The illumination path 5 sends the light through a set of color filters configured with/without masks (filter 15) that configures a set of fixation targets that comprise a first fixation target 35 and a second fixation target 40 displayed in an image plane 30 of the retina conjugate of a first plane 17 with certain optical characteristics (e.g., different colors or different polarities).

In various exemplary embodiments, the fixation targets 35, 40 can be configured in any number of different patterns and may include at least two sections with distinct spectral or polarization states. In various alternate embodiments, the fixation targets may be configured as a static display configured by bandpass filters or polarizers. In either case, the fixation targets are generated by integrating a pair of matching bandpass filters or polarizers at the retinal conjugate 17 (first plane) and also at the pupil conjugate 23 (second plane) with the use of apertures such as pinholes for the display of the pupil plane (third plane) 76. The illumination footprint 77 defined by the 2 pinholes (endpoints) is slightly overstretched to the footprint of the illumination light at the retina 70.

In various exemplary embodiments, the set of fixation targets (35, 40) is used to orient the gaze direction of a subject to a particular direction for the eye alignment (in 2 degrees of freedom). The fixation targets 35 and 40 are presented through the optics of the ophthalmologic device 110 to the same eye being imaged. The fixation targets 35, 40 may be moved laterally relative to the field of view of the ophthalmologic device 110 to guide the subject such that different parts of the retina 70 are within the system's field of view. The fixation targets 35, and 40 are presented such that they are in focus for the subject, and may be configured with at least some feature with a small angular extent such that the subject may orient his and her gaze direction with high precision.

In various embodiments, the ophthalmologic device 110 may be relatively immobile, and the subject moves their eye to meet the relatively static instrument pupil, similar to a desktop microscope. The device may have controls that the subject may manipulate to align a device pupil towards the pupil of their eye, similar to a traditional fundus camera. The device may be a handheld device in which the subject moves into place and controls position with their hands, similar to a pair of binoculars or a spyglass. The ophthalmologic device 110 may include a chin rest and/or forehead rest to support the patient relative to the instrument. The device could have one or more eye cups that come in contact with the subject and surround the subject's eye(s). Such an eye cup could be a permanent part of the ophthalmologic device 110 or could be a disposable part. The eye cup could have more sensors that are operably connected to the processor 95.

When both fixation targets 35 and 40 are visible to the subject, the ophthalmologic device 110 is properly centered. for example, the light from fixation targets 35 and 40 is transmitted via an objective lens 20 which may be any state-of-the-art lens including but not limited to a refractive, diffractive, reflective, or hybrid lens. The objective lens 20 is configured to project the display target at infinity through the pinholes in the pupil conjugate plane 23. And the pupil relay lens 45 is to image the pinholes in the pupil conjugate plane 23 to the subject pupil 65 (i.e., the imaging pupil 79).

The objective lens 20 may also be a source of various image artifacts (e.g., light reflections) as the illumination light (i.e., the light with the set of characteristics configured by the filter 15) passes through the objective lens 20. To compensate for or reduce the reflexes experienced or other aberrations caused by the objective lens 20, another set of color filters 25 with aperture masks (pinhole masks) is placed in illumination path 5 to further filter and constrain the light rays. Hence, the illumination path 5 to effectively remove any artifacts or interferences in light transmission between the objective lens 20 implements a dual configuration of filters of a first set of filters 15 and the second set of filters 25 that better eliminates out-of-focus light and allows for better capture by the image sensor 85 (of the camera 90) of point locations on the retina 70 associated with the set of fixation targets 35, 40.

In the implementation, the second set of filters 25 configures a second plane of the pupil conjugate 23 that spatially filters the light transmission for each fixation target 35 and 40 in which the light rays have been previously filtered by the first set of filters 15. The first set of filters 15 is configured to optically filter the spatially filtered light from the configured fixation target with an associated first optical characteristic (frequency, polarity, color, etc.) while the second set of filters 25 is configured to repeat the filtering process, consistent with the frequency, color or polarity applied to the light transmission from the first set of filters 15 to provide another step of optical filtering in approximately the same plane in which the spatial filtering is performed.

Next, the light is received by a pupil relay lens 45 in illumination path 5 for imaging the spatially filtered light on a third plane comprising the imaging plane (pupil plane) of the pupil 65. When the images of the first and second apertures in the second plane (pupil conjugate 23) are not vignetted by the pupil because the pupil is properly aligned, the fixation targets 35, 40 subsequently are imaged in the retinal plane that corresponds approximately to a field of view (FOV) of the retina 70 by redirection of the light (by the fold mirror 50) via the transmission path to a beam splitter 55 and then towards the apertures of the retina 70. The beam splitter 55 is configured to transmit light from the light source 10, to reflect light having an optical characteristic configured by the filter 15, and to reflect light having an optical characteristic of the filter 25. Light from the beam splitter 55 is captured by the image sensor 85 of the camera 90 and subsequently processed by the processor 95 to the display 97 via the GUI 99. Hence, the image sensor 85 captures light from the light source 10 that has entered the apertures of the pupil and has been reflected back or scattered by the subject's retina 70 thereby exiting the subject's pupil and received by the image sensor 85. The light from light source 10 configures a line segment (i.e., the illumination footprint 77) in the third plane. The line segment is approximately the width of the pupil and can range from about 1.8 mm (about 0.07087 inches) to about 2.0 mm (about 0.07874 inches).

In various embodiments, each fixation target 35, 40 can be considered a light source that generates either coherent or non-coherent light.

In various embodiments, the objective lens 20 is disposed between the first and second planes to project the first and second fixation targets at infinity through the first and second apertures of the filter 25.

The display 97 may include a graphical user interface 99 that enables configuration of the camera and image sensor operation that obtains the OCT or fundus image.

If the ophthalmologic device is misaligned with the subject's retina 70, the image displayed to the subject that includes either fixation target generated by the reflections of light is blocked by the pupil 65.

Additionally, in illumination path 5 a lens system 60 is positioned close to the eye 75 between beam splitter 55 and pupil 65 to focus the light rays configured with characteristics from both filters 15, and 25 towards the eye apertures.

In various embodiments, the processor 95 may comprise several processors or one processor with several processor cores may also be provided. The processor 95 is connected with a memory, for example a memory with a random access (RAM), or a non-volatile memory such as a flash memory or combinations thereof. Data and programs to operate the processor 85 and the ophthalmologic device 110 may be stored in the memory. In particular, different application programs (apps) may be stored in the memory, for example imaging and assessment applications related to the ascertain aperture alignment and configuration of fixation targets.

The processor 95 is further connected to a display 97 through which information, images, graphics and the like can be displayed for viewing by a user and may also be connected to a network interface for data exchange and may, for example, a mobile phone interface for communication through a mobile phone network, a Bluetooth interface or a Wi-Fi/WLAN interface for one or more types of remote operation and transfer of aperture alignment related information.

Figure 2A:
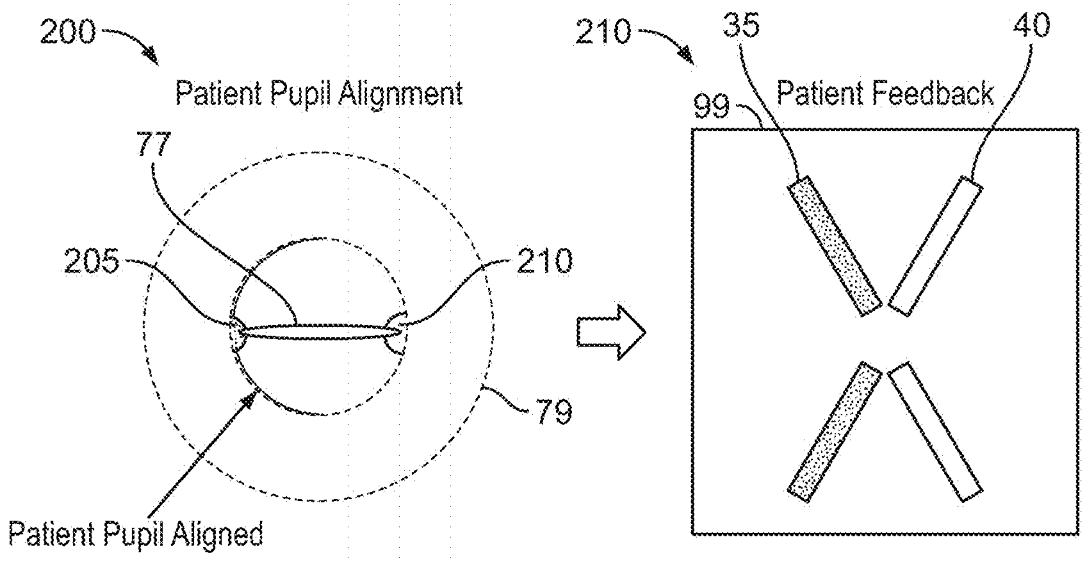
FIG. 2A illustrates a diagram of the subject's pupil alignment and a corresponding feedback display of fixation targets displayed to the subject in accordance with various embodiments.

FIG. 2A illustrates a diagram of the subject's pupil alignment and a corresponding feedback display of fixation targets displayed to the subject in accordance with various embodiments. In FIG. 2A, the subject pupil alignment is shown in the pupil conjugate or third plane 200 with characteristics from both sets of filters 15, 25 showing a complete illumination footprint 77 with both endpoint and circles 205, 210 in the pupil imaging 79. The camera image sensor 85 captures the reflected light from the retina and determines via the processor 95 (i.e., triggers a mechanism for determining an acceptable alignment) that the alignment is correct. For example, the processor 95 may determine that a sufficient FOV or point spread has been collected. Once this determination has been made, the subject has displayed the feedback in a graphical user interface 99 both fixation targets 35, and 40 as feedback that the alignment is correct. Each fixation target 35, and 40 make up parts of a cross and are of different colors. While the disclosure illustrates a cross-shape figure that represents both fixation targets, the disclosure is not limited to this shape or configuration, and a plethora of other indicators are contemplated as fixation targets including labels as well as audible and other notifications.

Figure 2B:
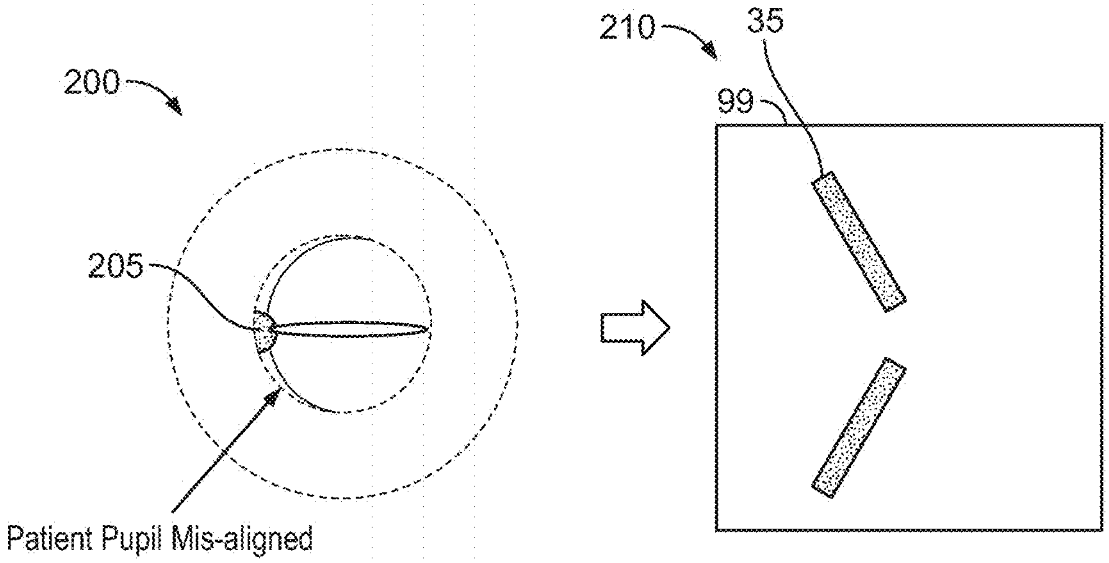
FIG. 2B illustrates a diagram of the subject's pupil misalignment and a corresponding feedback display of fixation targets displayed to the subject in accordance with various embodiments.

FIG. 2B illustrates a diagram of the subject's pupil misalignment and a corresponding feedback display of fixation targets displayed to the subject in accordance with various embodiments. In FIG. 2B, only a single endpoint or circle 205 is captured by the reflected light at the image sensor 85. The pupil imaging 79 of the third plane 200 shows that the illumination footprint 77 is off-center. In response, only one of the fixation targets 35, and 40 is displayed. In this case, the fixation target 35 is displayed corresponds to the endpoint or circle 205 to notify the subject that the alignment is laterally off-center towards the left side. Here, the subject is made aware that based on the feedback displayed to adjust via lateral movement of their eye 75 toward the left to cause the other fixation target to be visible. Further, the intensity of each fixation target may be modulated to instruct the subject in which direction to laterally correct for the alignment.

Figure 3A:
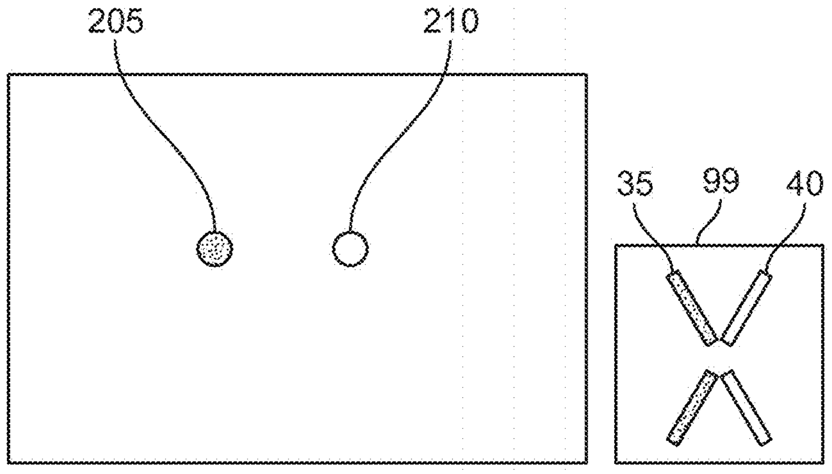
FIGS. 3A, 3B, 3C, and 3D illustrate diagrams of various approaches and states of the pupil plane using a coherent light from a laser as the light source in accordance with various embodiments.
Figure 3B:
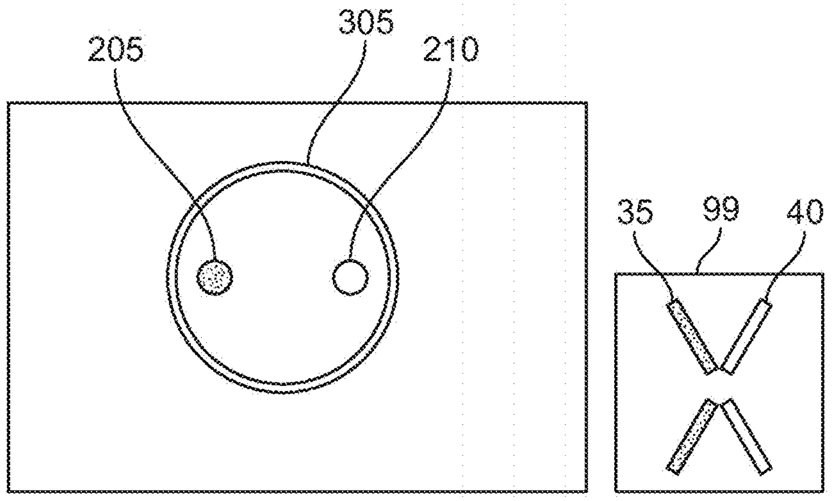
Figure 3C:
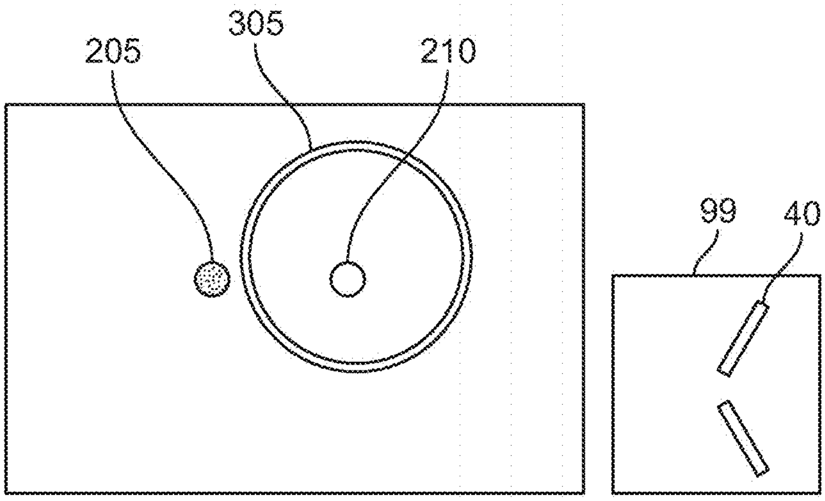
Figure 3D:
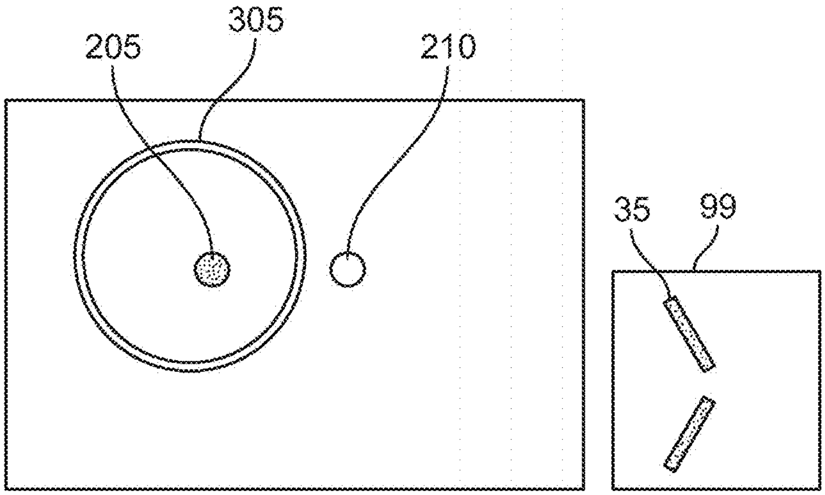
Figure 4:
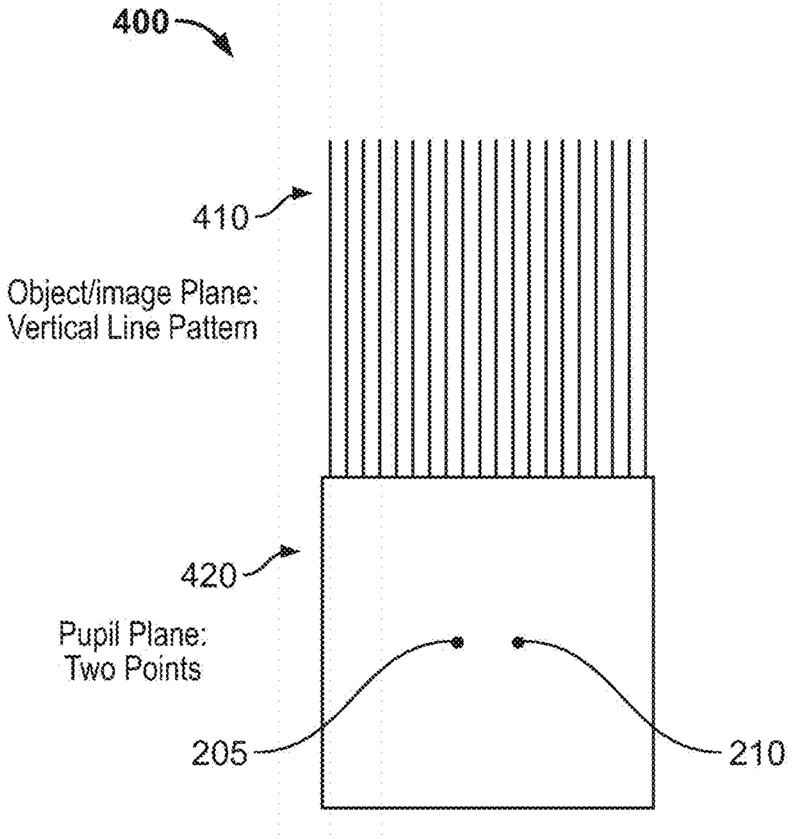
FIG. 4 illustrates another approach to pupil self-alignment that implements a feedback display of a vertical pattern or a uniform background if the pupil's aperture is aligned or not aligned to the ophthalmologic device in accordance with various embodiments.

FIGS. 3A, 3B, 3C, and 3D illustrate diagrams of various approaches and states of the pupil plane using a coherent light from a laser as the light source in accordance with various embodiments. In FIG. 3A, a blocking filter is configured in illumination path 5 from light source 10 containing coherent light via a laser transmitted to the retina 70. Here, the blocking filter may be configured with filter 15 or 25, or both, and acts like a camera's F stop to block certain bandwidths of transmitted light to cause only apertures (pinholes) that comprise different frequencies for different colors of reflected points or circles to be captured by the image sensor 85. If both points are captured by the image sensor 85, then the processor 95 displays both fixation targets 35, and 40 indicating proper alignment. In FIG. 3B, similar to the implemented blocking filter state of coherent light in FIG. 3A except that the pupil aperture is represented as a circle 305. Here if the subject views both circles 205 and 210 in circle 305 or views both fixation targets, then the alignment is correct. In FIG. 3C, if the coherent reflected light only shows a single circle 210 in the circle 305 then a corresponding single fixation target 40 is shown and the subject can determine that the pupil aperture is not in alignment. Here, the pupil aperture is off-centered to the right. Likewise, in FIG. 3D, a single circle 205 is displayed within circle 305 and the pupil aperture can be determined by the subject to be off-centered in the other direction to FIG. 3C, to the left. Again, the circle 205 displayed corresponds in color to the fixation target 35 displayed FIG. 4 illustrates another approach to pupil self-alignment that implements a feedback display of a vertical pattern or a uniform background if the pupil's aperture is aligned or not aligned to the ophthalmologic device in accordance with various embodiments. The approach with the feedback display of FIG. 4 operates in a similar manner to the approach described in FIG. 1 but does not require a filter 15 in a pupil conjugate plane. In FIG. 4, in diagram 400, the imaging of a vertical sine pattern (vertical pattern 410) is displayed if two points (i.e., two circles) are in the pupil plane. If the pupil plane only covers one of the two points, then the image will be a uniform background 420 without vertical lines.

In FIG. 4, a feedback display uses the second light source 12 (in FIG. 1) or source of coherent light. Here, the source of coherent light is located in a first plane 17 transmitting light in the retinal plane, and similarly, in the second plane, the pupil conjugate plane (or pupil plane) 23 configured with a first and second aperture (filter 25) that also is to spatially filter the coherent light transmission to image both apertures via the pupil relay lens 45 to the third plane 76, the pupil plane. If the ophthalmologic device is misaligned with the subject's pupil in approximately the third plane, the subject's pupil blocks the image of at least one of the first and second apertures transmitted via the filter 25 such that the subject's retina receives light from at most one of the first and second apertures. If the ophthalmologic device is aligned with the subject's pupil in approximately the third plane (pupil plane) 76, then the subject's pupil substantially transmits the images of the first and second apertures (circles 205, 210) such that the subject's retina receives an interference pattern generated by light from the first and second apertures (circles 205, 210). This interference pattern is shown to the subject in a feedback display in FIG. 4 of a uniform background 420 by the capture of the reflected light from the coherent light source 12 by the image sensor 85. If the aperture is aligned and the subject's pupil, in which most of the reflexed light is not blocked by the subject's pupil, the amount of reflected light captured by the image sensor 85 enables the processor 95 to determine that the aperture of the pupil is correctly aligned. In this case, a feedback display in the image plane is configured as a vertical pattern 410. If the subject's retina receives light from at most one of the first and second apertures of the filter 25, the subject's retina receives a uniform (color) background 420.

The objective lens is to project the display target at infinity through the pinholes. And the pupil relay lens is to relay the pinholes on top of the subject pupil (system exit pupil).

Figure 5:
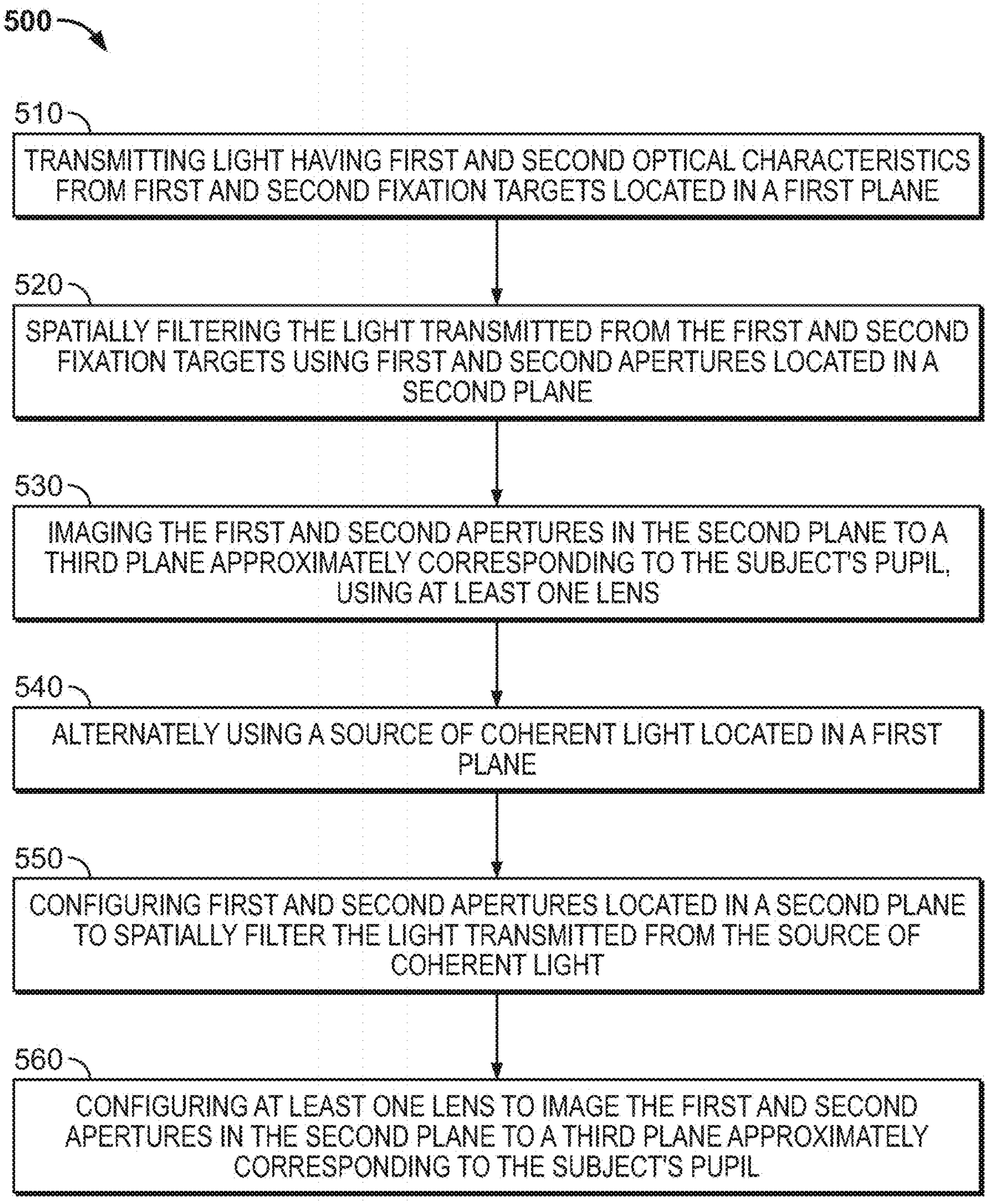
FIG. 5. Illustrates a flowchart of the operation of the fixation module of FIG. 1 integrated into an OCT, fundus imaging, or other ophthalmologic devices in accordance with various embodiments.

FIG. 5. Illustrates a flowchart of the operation of the fixation module of FIG. 1 integrated into an OCT, fundus imaging, or other ophthalmologic devices 110 in accordance with various embodiments.

The flowchart 500 illustrates steps for the process of assisting a subject with alignment with an ophthalmologic device. At step 510, a light source transmits light rays on illumination path 5 via a first filter 15 that is configured with a set of first and second optical characteristics from first and second fixation targets located in the first plane of the retina conjugate. At step 520, filter 25 is configured in illumination path 5 to spatially filtering the light transmitted from the first and second fixation targets using first and second apertures located in a second plane of the pupil conjugate. In this case, spatially filtered light from the first fixation target is configured to have the first optical characteristic, and the spatially filtered light from the second fixation target is configured to the second optical characteristic. Next at step 530, the imaging via the pupil relay lens 45 from the first and second apertures in the second plane to a third plane approximately corresponding to the subject's pupil is performed. If the ophthalmologic device 110 is misaligned with the subject's pupil in approximately the third plane, the subject's pupil blocks the image of the first and second apertures such that the subject's retina receives an image of at most one of the first and second fixation targets. Alternately, if the ophthalmologic device 110 is aligned with the subject's pupil in approximately the third plane, the subject's pupil substantially transmits the images of the first and second apertures such that the subject's retina receives an image of the first and second fixation targets. In this case, substantially all of the light from the first light source of the ophthalmologic device that enters the subject's pupil is reflected or scattered by the subject's retina, exits the subject's pupil, and is received by the image sensor 85.

At step 540, an alternate embodiment is implemented that uses a source of coherent light located in the first plane. In this case, at step 550, incoherent light is transmitted via first and second apertures located in a second plane that is configured to spatially filter the light transmitted from the source of coherent light. At step 560, a pupil relay lens 45 is configured to image the first and second apertures in the second plane to a third plane approximately corresponding to the subject's pupil. If the ophthalmologic device 110 is misaligned with the subject's pupil in approximately the third plane, the subject's pupil blocks the image of at least one of the first and second apertures such that the subject's retina receives light from at most one of the first and second apertures. If the ophthalmologic device 110 is aligned with the subject's pupil in approximately the third plane, the subject's pupil substantially transmits the images of the first and second apertures such that the subject's retina receives an interference pattern generated by light from the first and second apertures, and light from the light source of the ophthalmologic device enters the subject's pupil, is reflected or scattered by the subject's retina, exits the subject's pupil, and is received by the image sensor. The interference pattern comprises a vertical line pattern. If the subject's retina receives light from at most one of the first and second apertures, the subject's retina receives a uniform color background.

In various exemplary embodiments, the self-alignment process enables the subject to view the complete fixation target only if their pupil is well aligned within the 2 pinhole images. Part of the fixation target corresponding to the color or polarization will be vignetted and disappear if the eye pupil is decentered and blocked the light from one of the pinholes. In various exemplary embodiments, other possible color or polarization combinations can also be implemented based on the described process flow. principle.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications, and variations as may fall within the spirit and scope of the appended claims.

The invention claimed is:

1. A system for assisting a subject with alignment with an ophthalmologic device comprising a first light source and an image sensor, the system comprising:

first and second fixation targets located in a first plane and respectively configured to transmit light having first and second optical characteristics;

first and second apertures located in a second plane and configured to spatially filter the light transmitted from the first and second fixation targets;

first and second filters located approximately in the second plane, the first filter configured to optically filter the spatially filtered light from the first fixation target to have the first optical characteristic, the second filter configured to optically filter the spatially filtered light from the second fixation target to have the second optical characteristic; and at least one lens configured to image the first and second apertures in the second plane to a third plane approximately corresponding to the subject's pupil, wherein, based upon the ophthalmologic device being misaligned with the subject's pupil in approximately the third plane, the subject's pupil blocks the image of at least one of the first and second apertures such that the subject's retina receives an image of at most one of the first and second fixation targets; and wherein, based upon the ophthalmologic device being aligned with the subject's pupil in approximately the third plane:

the subject's pupil substantially transmits the images of the first and second apertures such that the subject's retina receives an image of the first and second fixation targets, and light from the first light source of the ophthalmologic device enters the subject's pupil, is reflected or scattered by the subject's retina, exits the subject's pupil, and is received by the image sensor.

2. The system of claim 1, wherein, in the third plane, the image of the first and second fixation targets forms a set of endpoints to the light from the first light source.

3. The system of claim 1, wherein the first and second optical characteristics comprise different colors than one another.

4. The system of claim 3, wherein the first and second fixation targets respectively comprise different color filters.

5. The system of claim 3, wherein the first optical characteristic comprises a red color and wherein the second optical characteristic comprises a blue color.

6. The system of claim 1, wherein the first and second filters respectively comprise different color filters.

7. The system of claim 1, wherein the first and second optical characteristics comprise different polarizations than one another.

8. The system of claim 7, wherein the first and second fixation targets respectively comprise different polarization filters than one another.

9. The system of claim 1, wherein the first and second filters respectively comprise different polarization filters.

10. The system of claim 1, wherein the light from the first light source comprises a line segment in the third plane.

11. The system of claim 10, wherein the line segment has a length that is approximately equal to a width of the subject's pupil.

12. The system of claim 11, wherein the length of the line segment is in a range of about 1.8 mm to 2.0 mm.

13. The system of claim 1, further comprising a second light source generating the light transmitted by the first and second fixation targets.

14. The system of claim 13, wherein the second light source generates coherent light.

15. The system of claim 13, wherein the second light source generates non-coherent light.

16. The system of claim 1, further comprising an objective lens disposed between the first plane and the second plane, the objective lens being configured to project the first and second fixation targets at infinity through the first and second apertures.

17. The system of claim 1, wherein the at least one lens comprises a pupil relay lens disposed between the second plane and the third plane, the pupil relay lens being configured to image the first and second apertures into the third plane.

18. The system of claim 1, further comprising a beam splitter configured to transmit light from the first light source, to reflect light having the first optical characteristic, and to reflect light having the second optical characteristic.

19. The system of claim 1, wherein the ophthalmologic device comprises an optical coherence tomography imager.

20. The system of claim 1, wherein the ophthalmologic device comprises a fundus imager.

21. The system of claim 1, further comprising at least one additional fixation target, at least one additional aperture, and at least one additional filter.

22. A method for assisting a subject with alignment with an ophthalmologic device, the method comprising:

respectively transmitting light having first and second optical characteristics from first and second fixation targets located in a first plane;

spatially filtering the light transmitted from the first and second fixation targets using first and second apertures located in a second plane;

optically filtering the spatially filtered light from the first fixation target to have the first optical characteristic;

optically filtering the spatially filtered light from the second fixation target to have the second optical characteristic; and imaging the first and second apertures in the second plane to a third plane approximately corresponding to the subject's pupil, using at least one lens, wherein, based upon the ophthalmologic device being misaligned with the subject's pupil in approximately the third plane, the subject's pupil blocks the image of at least one of the first and second apertures such that the subject's retina receives an image of at most one of the first and second fixation targets; and wherein, based upon the ophthalmologic device being aligned with the subject's pupil in approximately the third plane:

the subject's pupil substantially transmits the images of the first and second apertures such that the subject's retina receives an image of the first and second fixation targets, and light from the first light source of the ophthalmologic device enters the subject's pupil, is reflected or scattered by the subject's retina, exits the subject's pupil, and is received by the image sensor.

23. A system for assisting a subject with alignment with an ophthalmologic device comprising a light source and an image sensor, the system comprising:

a source of coherent light located in a first plane;

first and second apertures located in a second plane and configured to spatially filter the light transmitted from the source of coherent light; and at least one lens configured to image the first and second apertures in the second plane to a third plane approximately corresponding to the subject's pupil, wherein, based upon the ophthalmologic device being misaligned with the subject's pupil in approximately the third plane, the subject's pupil blocks the image of at least one of the first and second apertures such that the subject's retina receives light from at most one of the first and second apertures; and wherein, based upon the ophthalmologic device being aligned with the subject's pupil in approximately the third plane:

the subject's pupil substantially transmits the images of the first and second apertures such that the subject's retina receives an interference pattern generated by light from the first and second apertures, and light from the light source of the ophthalmologic device enters the subject's pupil, is reflected or scattered by the subject's retina, exits the subject's pupil, and is received by the image sensor.

24. The system for self-alignment of an ophthalmologic device of claim 23, wherein the interference pattern comprises a vertical line pattern.

25. The system for self-alignment of the ophthalmologic device of claim 23, wherein when the subject's retina receives light from at most one of the first and second apertures, the subject's retina receives a uniform color background.

26. A method for assisting a subject with alignment with an ophthalmologic device comprising a light source and an image sensor, the system comprising:

spatially filtering coherent light transmitted from a source in a first plane using first and second apertures located in a second plane; and imaging the first and second apertures in the second plane to a third plane approximately corresponding to the subject's pupil, wherein, based upon the ophthalmologic device being misaligned with the subject's pupil in approximately the third plane, the subject's pupil blocks the image of at least one of the first and second apertures such that the subject's retina receives light from at most one of the first and second apertures; and wherein, based upon the ophthalmologic device being aligned with the subject's pupil in approximately the third plane:

the subject's pupil substantially transmits the images of the first and second apertures such that the subject's retina receives an interference pattern generated by light from the first and second apertures, and light from the light source of the ophthalmologic device enters the subject's pupil, is reflected or scattered by the subject's retina, exits the subject's pupil, and is received by the image sensor.

* * * * *